United States Patent [19]
Simmons et al.

[11] Patent Number: 6,051,394
[45] Date of Patent: Apr. 18, 2000

[54] DETECTION OF MICROORGANISMS

[76] Inventors: Maxine Helen Simmons, 229 Amreins Road, Taupaki, Auckland 1009; Rosemary Katherine Cameron Sharpin, 74 Arney Road, Remuera, Auckland 1005, both of New Zealand

[21] Appl. No.: 09/254,801
[22] PCT Filed: Sep. 12, 1997
[86] PCT No.: PCT/NZ97/00116
  § 371 Date: Mar. 11, 1999
  § 102(e) Date: Mar. 11, 1999
[87] PCT Pub. No.: WO98/11250
  PCT Pub. Date: Mar. 19, 1998

[30]  Foreign Application Priority Data

Sep. 13, 1996 [NZ] New Zealand .............................. 299386
Jul. 25, 1997 [NZ] New Zealand .............................. 328426

[51] Int. Cl.[7] .............................. C12Q 1/02; C12Q 1/22; C12Q 1/18
[52] U.S. Cl. .............................. 435/29; 435/31; 435/32; 435/283.1; 435/975
[58] Field of Search .............................. 435/29, 31, 32, 435/283.1, 975

[56]  References Cited

U.S. PATENT DOCUMENTS

| | | | |
|---|---|---|---|
| 4,203,440 | 5/1980 | Theeuwes | 435/29 |
| 5,344,761 | 9/1994 | Citri | 435/29 |
| 5,420,017 | 5/1995 | Tuompo et al. | |
| 5,429,803 | 7/1995 | Guirguis | |
| 5,635,362 | 6/1997 | Levine et al. | |

FOREIGN PATENT DOCUMENTS

| | | |
|---|---|---|
| 0254771 | 2/1986 | European Pat. Off. |
| 0244148 | 11/1987 | European Pat. Off. |
| WO9403632 | 2/1994 | WIPO |
| WO9638584 | 12/1996 | WIPO |

OTHER PUBLICATIONS

"Growth in Nitrogen–Free Mineral Salts Medium," Microbiological Techniques Manual, School of Microbiology, University of Melbourne, pp. 91–92.

Brock, Thomas D., "Steps in the Identification of an Unknown Bacterial Culture," Biology of Microorganisms, pp. 607–609, 1979.

"Eosin Methylene–blue Lactose Sucrose Agar EMB Agar," Handbook of Microbiology (Merck), pp. 173–174, 1983.

"Fuchsin Lactose Agar acc. to Endo (Type C) Endo C Agar," Handbook of Microbiology (Merck), pp. 175–176, 1983.

"Fuchsin Lactose Agar acc. to Endo (Type S) Endo S Agar," Handbook of Microbiology (Merck), pp. 177–178, 1983.

*Primary Examiner*—Louise N. Leary
*Attorney, Agent, or Firm*—Webb Ziesenheim Logsdon Orkin & Hanson, P.C.

[57]  ABSTRACT

A method and kit for detecting micro-organisms in a mass or liquid or on a surface. The method is conducted by obtaining a sample and within a sterile chamber of limited volumetric capacity placing the sample in contact with a composition adapted to detect micro-organisms. The sterile chamber may contain a filter for isolating any micro-organisms present in the sample. Sterile sampling instruments, a delineating instrument and means for typing the micro-organisms may also be provided.

11 Claims, 5 Drawing Sheets

INCUBATION → RECORD CHANGES

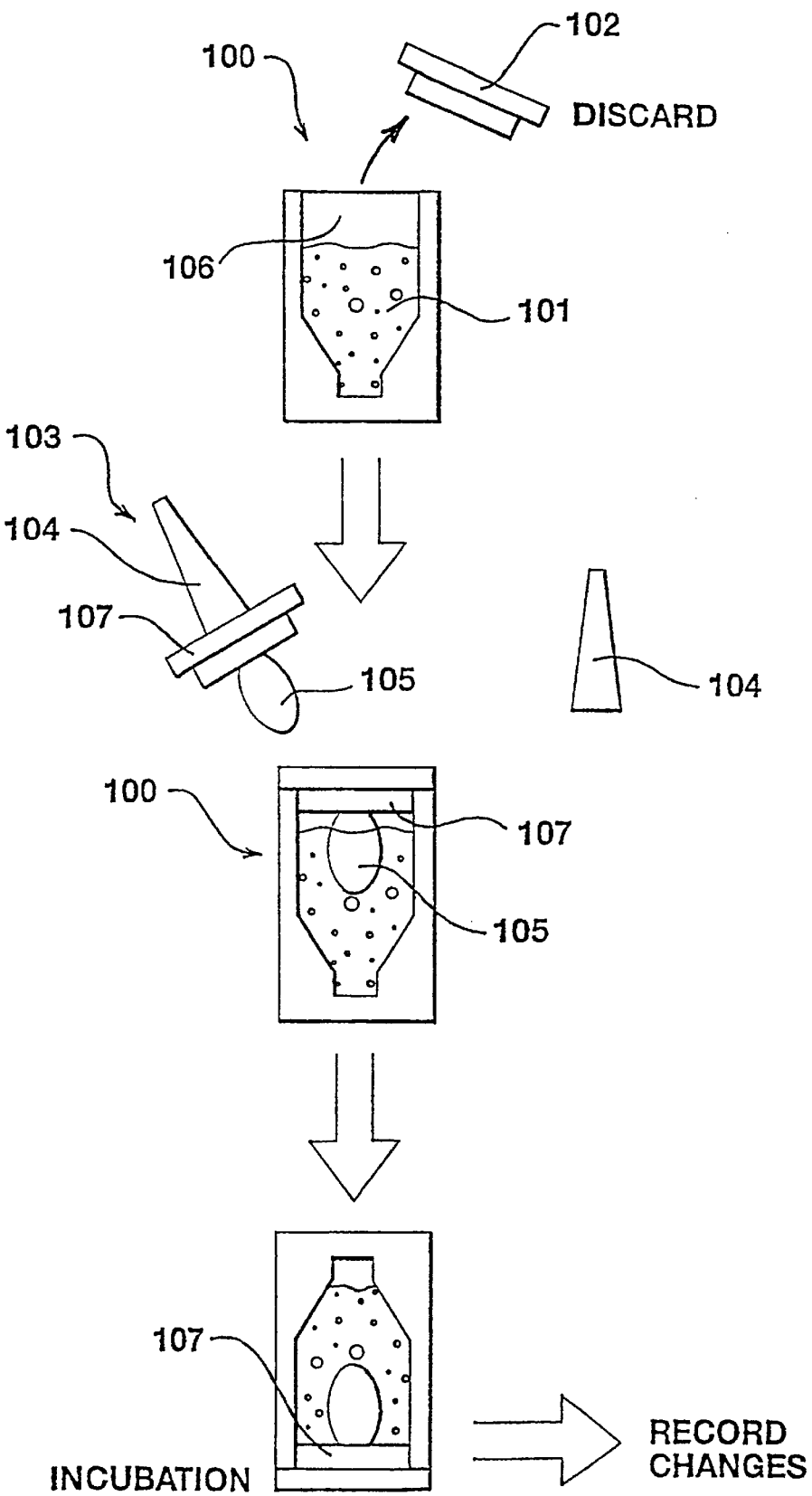

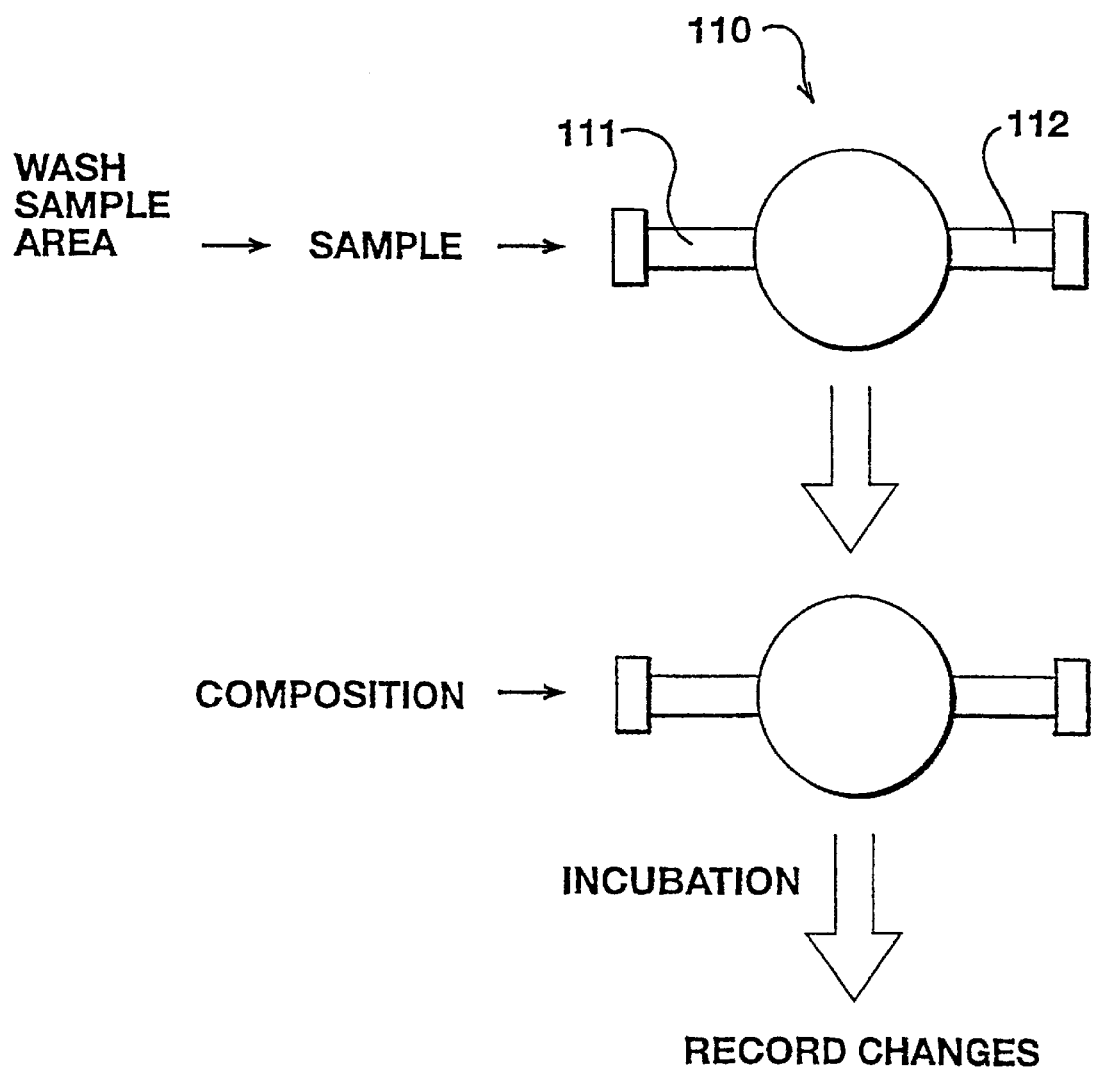

DETECTION OF MICROORGANISMS

BACKGROUND OF THE INVENTION

1. Field of the Invention

This invention relates to the detection of micro-organisms and is particularly, but not exclusively, applicable to the detection of pathogenic micro-organisms during the preparation of food for human consumption.

2. Description of the Related Art

The contamination of foodstuffs, cosmetics, pharmaceuticals and the like by undesirable micro-organisms represents a significant threat to public health. In the past a number of methods to monitor the presence of such micro-organisms in foodstuffs, water supplies and on food preparation surfaces for example have been developed. Generally, such methods rely on conventional microbiological techniques, typically including the growth of micro-organisms on selective nutrient solid support media or alternatively in selective nutrient media. Subsequent morphological analyses are carried out. Such testing techniques are hindered by the fact that a result may not be obtained for 24 to 48 hours or more and the process is complex and laborious.

The demand for simple tests in which results as to the number of particular pathogenic micro-organisms present in a sample can been obtained in less time than the above described tests has lead to the development of alternative techniques. Such techniques are based on the growth of micro-organisms in nutrient media in the presence of an indicator specific to a micro-organism that is to be detected, or alternatively in selective growth media. A period of approximately 12 to 24 hours is still required for a result to be obtained in such testing assays. Generally, during all aspects of the preparation of food for human consumption and the like this time constraint is undesirable.

Other possible problems associated with the current assay systems available for detecting pathogenic micro-organisms may include the lack of containment of the micro-organism during the detection process and in the case of testing food preparation surfaces for example the standardisation of the sample area.

It is an object of the present invention to provide an improved means and method of detecting micro-organisms, or one which will at least provide the public with a useful choice.

SUMMARY OF THE INVENTION

According to one broad aspect of the present invention there is provided a method of detecting micro-organisms comprising the steps of taking a sample from a mass, surface or a fluid to be tested, providing a sealable sterile chamber of substantially limited volumetric capacity in which the detection process is to be conducted, placing the sample in contact with a composition capable of detecting micro-organisms within said sealable sterile chamber and recording a change in the composition.

Preferably the volumetric capacity of said sealable sterile chamber is less than 10 cubic centimeters.

More preferably volumetric capacity of said sealable sterile chamber is less than or equal to 2 cubic centimeters.

Preferably the sample is taken and is placed in contact with said composition in said sealable sterile chamber using a sterile sampling instrument.

Alternatively the sample is taken by washing the surface with an appropriate solution and subsequently collecting the wash solution.

Alternatively the sample is taken from the surface using a sterile sampling instrument, the sterile sampling instrument washed with an appropriate solution and subsequently collecting the wash solution.

Alternatively the sample is taken by removing a mass from an object to be tested, washing the mass with an appropriate solution and subsequently collecting the wash solution.

Preferably said change in the composition capable of detecting micro-organisms is one which can be visualised by eye or in a spectrophotometer.

Preferably the method described in any of the preceding 8 paragraphs further comprises the step of delineating an area of a surface to be tested and placing the sterile sampling instrument in contact with substantially all of the delineated area.

Preferably the method described in any of the preceding 9 paragraphs further comprises the initial step of removing any extraneous matter from said sample.

More preferably the method described in any of the preceding 10 paragraphs further comprises a final step of typing any micro-organisms detected.

In a related aspect of the present invention there is provided a method for detecting micro-organisms according to paragraph 1 above including the steps of taking a sample from a mass, surface or a fluid to be tested, providing a sealable sterile chamber, placing the sample in the sealable sterile chamber, substantially isolating any micro-organisms present in the sample by filtration within the sealable sterile chamber, placing the isolated micro-organisms in contact with a composition capable of detecting micro-organisms within sealable sterile chamber, and recording a change in the composition.

In a further related aspect of the present invention there is provided a method for detecting micro-organisms according to paragraph 1 above including the steps of providing a delineating instrument, delineating an area of a surface to be tested, providing a sterile sampling instrument, placing the sterile sampling instrument in contact with substantially the whole of the delineated area to be tested, washing said sterile sampling instrument in an appropriate solution, providing a sealable sterile chamber, placing the wash solution in said sealable sterile chamber, substantially isolating any micro-organisms present in the wash solution by filtration within the sealable sterile chamber, placing the isolated micro-organisms in contact with a composition capable of detecting micro-organisms within sealable sterile chamber, and recording a change in the composition.

In a further related aspect of the present invention there is provided a method for detecting micro-organisms as described in paragraph 1 above including the steps of providing a sterile sampling instrument, taking a sample of from a mass, liquid or surface to be tested, providing a sealable sterile chamber containing a defined amount of a composition capable of detecting micro-organisms, placing at least a part of the sterile sampling instrument and thus the sample in contact with the composition, and recording a change in the composition.

In a further related aspect of the present invention there is provided a method for detecting micro-organisms as described in paragraph 1 above including the steps of providing a delineating instrument, delineating an area of a surface to be tested, providing a sterile sampling instrument, placing the sampling instrument in contact with substantially the whole of the delineate area of the surface to be tested, providing a sealable sterile chamber containing a defined amount of a composition capable of detecting micro-organisms, placing at least a part of the sterile sampling instrument and thus the sample in contact with the composition, and recording a change in the composition.

According to another aspect of the present invention there is provided a kit for the detection of micro-organisms according to the method described in the preceding 15 paragraphs comprising a sealable sterile chamber, a defined amount of a composition adapted to detect micro-organisms, and a means for collecting and placing a sample in contact with said composition adapted to detect micro-organisms.

Preferably the composition is provided in said sealable sterile chamber.

Preferably at least a part of the sealable sterile chamber is translucent.

More preferably the sealable sterile chamber contains a means for substantially isolating any micro-organisms in the sample.

Preferably the sealable sterile chamber is a filter unit.

Preferably the filter unit contains a membrane filter with a pore size of about 0.2 microns or less.

Alternatively the sealable sterile chamber is a cuvette.

In a related aspect of the present invention there is provided a kit according to the preceding 7 paragraphs further comprising any one or more of: a sterile sampling instrument, a sterile template to delineate an area of a surface to be tested, a means for removing extraneous matter from the sample prior to the sample being placed in contact with said composition adapted to detect micro-organisms and a means of substantially determining the number of micro-organisms in the sample.

Preferably the sterile sampling instrument is a swab device containing a handle and a detachable head supporting a swab.

Preferably the head of the sterile sampling instrument is adapted to co-operate with the mouth of the sealable sterile chamber to form a seal between said head and said mouth so that in use said swab is contained inside said sealable sterile chamber.

Preferably the delineating instrument is an area defining template.

Alternatively the sterile sampling instrument may delineate the area of a surface to be tested.

Preferably the means for removing extraneous matter from a sample prior to placing the sample in contact with the composition capable of detecting microorganisms is a filtration system comprising one or more filter units.

Preferably the means of substantially determining the number of micro-organisms in the sample is a colour chart or the like.

Preferably the composition adapted to detect micro-organisms is as herein described.

In a further related aspect of the present invention there is provided a selective composition for the detection of micro-organisms containing an indicator, an inhibitor of non-specific micro-organisms, a protein source, and an energy source.

BRIEF DESCRIPTIONS OF THE DRAWINGS

Various embodiments of the current invention are described, by way of example only, with reference to the accompanying drawings, in which:

FIGS. 1A to 1C are diagrammatic representations of the apparatus and method of the first preferred embodiment of the invention;

FIGS. 2A and 2B are diagrammatic representations of the apparatus and method of the second preferred embodiment of the invention.

DETAILED DESCRIPTION OF THE PREFERRED EMBODIMENT

Preferred Assay Compositions

Figure 1A:
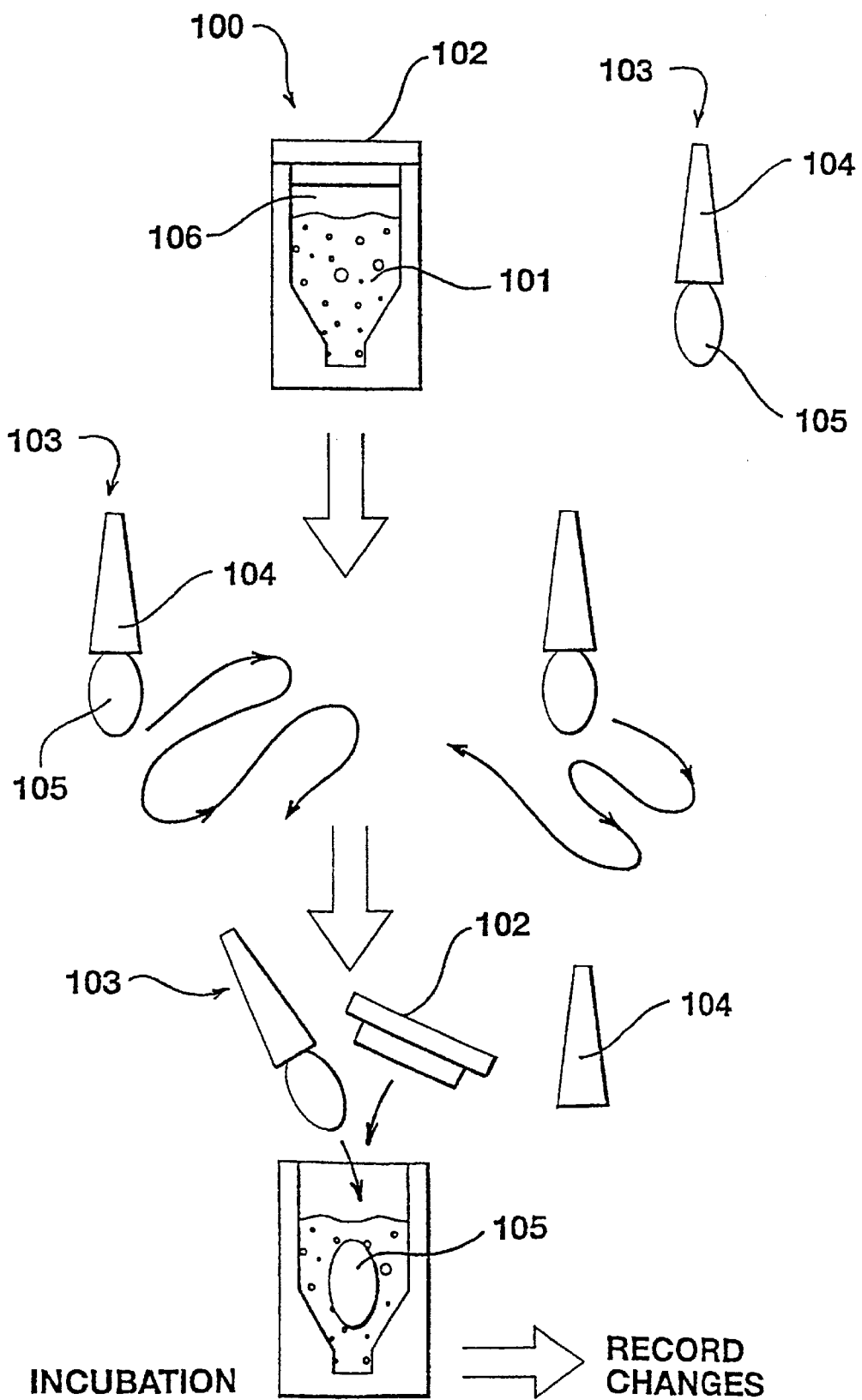

The following description of the preferred embodiments of the present invention make reference to assay compositions. Examples of the preferred compositions are given in the tables below. It should be noted, that these assay compositions may be altered to allow for the specific growth and detection of various microorganisms; the present examples relate to the detection of coliform bacteria (Table 1 and Table 2) and staphylococcal bacteria (Table 3).

EXAMPLE 1

Coliform Bacteria

One preferred assay composition of the present invention contains an indicator (eg Resazurin), an inhibitor (eg Bile Salts) of non-specific micro-organisms (ie those micro-organisms not being tested for), a protein source (eg Casitone), an energy source (eg lactose), and at least one salt (eg NaCl). An example of this composition is described below; Table 1. In addition, a range of the percentage of each component of the composition has been given within which the detection of coliforms may still be carried out under the present invention. A further specific example of an assay composition is given in Table 2.

TABLE 1

| Component | Percentage (w/v) | Range (% w/v) |
| --- | --- | --- |
| Lactose | 3 | 0.5–10 |
| Bile Salts | 0.44 | 0.1–1.0 |
| Casitone | 0.2 | 0.02–1.0 |
| NaCl | 0.643 | 0.4–1.0 |
| KCl | 0.037 | 0.01–0.06 |
| $CaCl_2$—$H_2O$ | 0.0184 | 0.01–0.03 |
| $MgCl_2$—$6H_2O$ | 0.0091 | 0.005–0.02 |
| Resazurin* | 0.00058 | 0.0001–0.01 |

*Resazurin is a redox dye indicator - other similar indicators could be used - for example Triphenyltetrazolium chloride (TCC) and Rosolic Acid (Table 3)
*Resazurin is also known as (7-Hydroxy-3H-phenoxazin-3-one 10-oxide) Sodium Salt and can be purchased from Sigma as Resazurin R-2127.

TABLE 2

| Component | Percentage (w/v) |
| --- | --- |
| Lactose | 1 |
| Bile Salts | 0.44 |
| Casitone | 0.2 |
| NaCl | 0.643 |
| KCl | 0.037 |
| $CaCl_2$—$H_2O$ | 0.0184 |
| $MgCl_2$—$6H_2O$ | 0.0091 |
| Resazurin* | 0.00058 |

EXAMPLE 2

Staphylococcal Bacteria

An example of the range of components used in an assay composition which may be used to support the growth and detection of staphylococcal bacteria is given below in Table 3.

TABLE 3

| Component | Percentage Range (w/v) |
| --- | --- |
| Bacto tryptone | 0.2–5.0 |
| Yeast extract | 0.1–0.5 |
| Lactose | 0.1–0.5 |
| Mannitol | 0.5–2.0 |
| dipotassium phosphate | 0.2–1.0 |
| Sodium Chloride | 5.0–10.0 |
| Rosolic Acid | 0.2–5.0 |

It should be noted that the components of the composition of Table 1, 2 or 3 may be varied depending on whether or not a sterile solution is used to wash the sample surface to be tested (see first and second preferred embodiments below) and the nature of such a solution. For example, if Butterfields Buffer was used to wash the surface to be tested the reaction composition would contain no supplementary sodium chloride as is present in the compositions of Table 1. Where meat samples are to be tested the composition of Table 1 preferably contains no salt. In addition, alternative redox dyes or other indicators may be utilised. Further, the protein, salt and energy sources of the compositions herein described may be altered to support the growth of various alternative micro-organisms.

First Preferred Embodiment

The following description is a preferred embodiment of the present invention as it relates to the detection of coliform bacteria on food preparation surfaces. This is given by way of example only and it should be understood that the method and apparatus of the invention may be adapted for the detection of any of a number of classes or types of micro-organisms on any of a number of surfaces or alternatively for use with liquid samples.

Firstly, a sterile reaction chamber 100 is provided containing approximately 100 $\mu$l–2000 $\mu$l of a reaction composition 101 as described above. This volume may be altered to accommodate modified applications. The sterile chamber is translucent or at least a part of it is translucent and is preferably of small volumetric capacity; for example, 10 cubic cm or less and preferably 2 cubic cm or less. Preferably the reaction chamber is a cuvette and more preferably a micro-cuvette is utilised. Such a reaction chamber contains a cap 102. The cap 102 may attach to the cuvette via a screw thread or other suitable attachment means. The cuvette may be constructed from plastic or other suitable materials; for example, if the change in the composition is to be measured on a spectrophotometer then the material from which the cuvette is constructed may be altered to correspond with the wavelength at which the measurement is to be taken. In this preferred embodiment the cuvette is constructed from perspex. In addition, the cap of the cuvette may contain a sample port through which samples of the assay composition before or after the test reaction is conducted may be taken for subsequent analysis.

Secondly, an aseptically packaged sterile sampling instrument 103 is supplied. In this preferred embodiment the sampling instrument is a swab device comprising a handle 104 and a head 105. The head supports a swab. The handle 104 is preferably constructed of plastic or other suitable material and the swab supported on the head from foam or other suitable material. In this embodiment the head 105 is detachable from the handle 104. Alternatively, at the base 107 of the detachable head 105, there is preferably includes a screw thread or the like attachment means which co-operates with the mouth 106 of the cuvette 100 to form a seal (and thus acts as a cap) and is adapted to hold the swab carried on the head 10 in place inside the cuvette 100; see FIG. 1B.

To perform the method of detection of micro-organisms according to the present embodiment of the invention the aseptically packaged sterile sampling instrument, or swab device 103, is removed from its packaging taking care not to touch the sterile head 105. One side of the head 105 of the swab 103 is placed in contact with the surface to be tested and moved over the surface. The swab device 103 may then be turned over and a second side of the head 105 of the swab device 103 is placed in contact with the surface to be tested. In this example the swab device 103 is moved over the surface in a manner which is perpendicular to the direction moved when the first side of the head 105 of the swab device 103 was placed in contact with the surface to be tested as illustrated in FIG. 1A. Other methods of dragging the swab device 103 over the surface to be tested may alternatively be used. For example, one may drag the head of the swab device 103 over an area to be tested and then turn the swab device over and drag the head 105 of the swab device 103 over a separate area of the same object being tested.

The cap 102 of the cuvette 100 is removed. The head 105 of the swab device 103 is placed in the mouth 106 of the cuvette 100 and the handle 104 of the swab device 103 is pulled away from the cuvette 100 in a horizontal manner so that the head 105 of the swab device 103 falls into the composition 101 contained within the cuvette 100. The cap 102 is then replaced and the cuvette 100 is shaken to ensure that the head 105 of the swab device 103 comes in complete contact with the composition 101. In a preferred alternative form of this embodiment (seen in FIG. 1B) the base 107 of the detachable head preferably includes a screw thread or the like attachment means which co-operattes with the mouth 106 of the cuvette 100 to form a seal (and thus acts as a cap) and is adapted to hold the swab carried on the head 105 in place inside the cuvette 100. In this cas the cuvette may be incubated upside down so that the swab on the head 105 of the swab device is submerged in the assay composition; FIG. 1B.

The cuvette 100 containing the composition 101 and the head 105 of the swab device 103 is incubated at a temperature specific to the micro-organism that the test is to identify. In this embodiment incubation takes place at 98° F. (37° C.). At this temperature all coliform bacteria are selected for. Alternatively one may choose to incubate at 113° F. (45° C.) to select for the growth of predominantly *E. coli* bacterium. The temperature may be altered to accommodate the growth of various other types of micro-organisms; eg if the presence of staphylococcal bacterium was desired incubation would take place in the media described in table 3 at 37° C. During incubation the composition 101 should be inspected occasionally and compared with a negative control (an unused cuvette containing the assay composition). Over time the composition will change in colour (if coliform bacteria are present in the sample), in this embodiment from blue to a red/pink colour. This colour change is a result of oxidation/reduction reactions involving a dye (Resazurin—see Tables 1 & 2) present within the composition. The rate at which this occurs will be dependent on the number of coliforms present in the initial sample taken (see Table 4). The time at which a colour change is observed compared with the negative control should be noted. Over the next 30–60 minutes the colour will change to a definite red/pink. It is preferable that approximation of the number of micro-organisms present in the original sample may be determined by comparison of the reaction colour with a colour chart.

Alternatively a spectrophotometer may be used to measure the colour change before it is visible by the eye. In this case, during the incubation period the cuvette 100 containing the composition and head 105 of swab device 103 can be directly placed in a spectrophotometer and absorbance measurements taken at 600 nm and 560 nm. A change in the ratio 600/560 nm compared with that of the negative control will indicate the presence of coliforms in the initial sample taken approximately 30 to 90 minutes before a colour change can be visualised by the eye. The time at which this occurs should be noted. By way of example, a change in the ratio 600/560 nm of more than 15% compared to the negative control will indicate the presence of 200 coliforms in the area sampled by 7 hours (see Table 4 for further examples).

TABLE 4

| Number of Coliforms | Time to Visualise Initial Colour Change by Eye (compared to control) (Hours) | Time for Complete Change to Red (Hours) | Spectrophotometer Time to Measure a Difference in the Optical Density of 0.03 or More (control compared to sample) (Hours) |
| --- | --- | --- | --- |
| 1,000,000 | 3.0 | 3.5–4.0 | 1.5 |
| 10,000 | 4.5 | 4.5–5.0 | 3.5 |
| 1,000 | 6.0 | 6.5–7.0 | 5.0 |
| 200 | 7.5 | 7.5–8.0 | 6.0 |

In this preferred embodiment of the invention the assay composition/(s) described in the previous section above (Preferred Assay Compositions) are applicable.

Figure 1C:
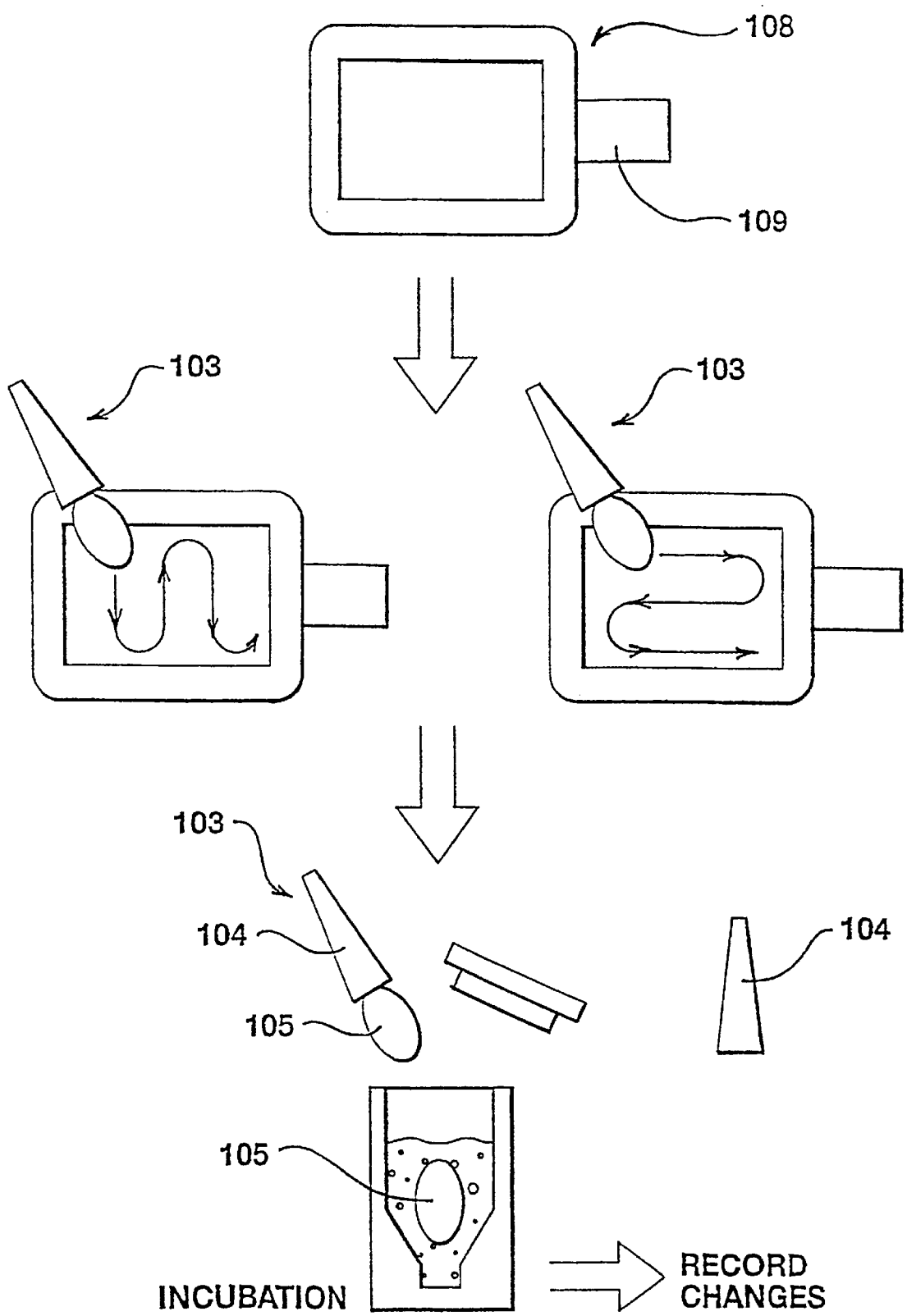

The above described apparatus and method may further comprise the use of a sterile template which delineates and thus standardises the sample area to be tested. In this preferred embodiment the template defines an area of 1 square inch however, this area could be altered to suit various other applications or to increase the sensitivity or speed of the assay. The template 108 may be constructed from plastic or other suitable material. It is preferable that the template contains a means for handling the template while substantially keeping it sterile; for example, the tab 109 of FIG. 1C. In use, the sterile template 108 is placed on a surface to be tested, for example a food preparation surface. The template 108 is preferably handled by tab 109 so as to keep the template substantially sterile. A sample from the area to be tested may be taken using the method and swab device above described; it is preferable that the swab contacts substantially the whole of the area defined by the template.

The above described method may be modified by the addition of a step in which following sampling of a surface with the swab device 103 the swab supported on head 105 is washed with an appropriate sterile solution (see previous section above) and a sample of this solution post washing is subsequently used in the detection assay. In this case the sample will be mixed with the assay composition contained within the cuvette 100 and the reaction allowed to continue as previously described. Preferably the assay composition will be provided in the cuvette 100 in a freeze dried state in this case. This method is also applicable where a swab is not used but the surface to be tested is washed in an appropriate solution or buffer (see previous section above) and the liquid sample is to be tested. Further, this method is applicable to the detection of micro-organisms in liquids, for example water supplies, laboratory preparations and beverages.

Second Preferred Embodiment

The following is a description of a second preferred embodiment of the present invention as it relates to the detection of coliform bacteria on food preparation surfaces. This is given by way of example only. However, as with the previously described embodiment, it should be understood that the method or apparatus of the invention may be adapted for the detection of any of a number of micro-organisms on any of a number of surfaces or alternatively liquid samples.

In this preferred embodiment of the invention the assay composition/(s) described in the previous section above (Preferred Assay Compositions) are applicable.

As indicated in FIG. 2 the area of a surface to be tested is initially washed with a suitable sterile solution such as water or an appropriate buffer (see example above under Preferred Assay Compositions). Such a surface may comprise a wide variety of objects; for example, a bench for preparation of food stuffs, cosmetics, pharmaceuticals and the like or food stuff itself eg animal carcasses. Also, a measured mass of a foodstuff (for example) to be tested may be washed with a suitable sterile solution. Alternatively, a fluid sample may be taken from a solution such as a water supply for example. Further, a swab device as described in the first preferred embodiment may be used to obtain a sample from a surface to be tested, washed in a suitable sterile solution and a sample of that solution post washing the swab device utilised in the present embodiment. A sample of the solution post washing the surface (or swab device), or the fluid sample itself, is then filtered through a sterile filter preferably with a pore size of 0.2 $\mu$m or less. The filter is preferably a membrane filter constructed of suitable filter materials such as cellulose ester, nitrocellulose, polyethylene, polysulfone, polycarbonate or the like. The filter is preferably enclosed in a translucent housing, or a housing at least part of which is translucent, constructed of plastics materials or the like and being of the type containing an inlet 111 and an outlet 112 spigot or the like as shown in FIG. 2A. This filter and housing forms the filter unit 110. The inlet spigot may preferably contain a one way valve. Further the filter unit 110 is preferably of relatively small volumetric capacity; for example less than 2 cubic cm.

The sample may be moved through the filter by any number of conventional methods: for example, injection, pumping. The means of passing the sample through the filter may depend on the size of the filter unit 110 and the nature and volume of the sample.

Following filtration any micro-organisms present in the sample solution will be supported on or in the filter membrane and contained within the filter unit 110.

Next, an appropriate volume of a composition used to detect a particular type of micro-organism is inserted, preferably by injection, into the filter unit 110 through either the inlet 111 or outlet 112 spigot and thus comes into contact with any micro-organisms supported on or in the filter. An example of such an appropriate volume of the composition of this preferred embodiment is 1 ml. The assay composition is preferably supplied in a sterile sealed container such as a syringe or plastic vial of a volumetric capacity of 1.5 to 2.0 ml.

The filter unit 110 containing the composition of this preferred embodiment and sample micro-organisms (if present in sample) is incubated at a temperature specific to the micro-organism that the test is to identify. In this embodiment incubation takes place at 98° F. (or 37° C.). Different temperatures may be used depending on the type of bacterium one wishes to detect. Incubation and recording of a colour change in the assay composition should be carried out according to that of the first preferred embodiment. Again, in this preferred embodiment a colour chart may be used at some time during or at the conclusion of the assay to indicate the number of microorganisms present in the initial sample solution; ie by comparing the colour of the test reaction at a given time with that of the colour chart.

In an alternative of the second preferred embodiment the method of detecting micro-organisms as described above may also include the step of employing a pre filtration system upstream of the filter unit 110 to remove any extraneous matter contained in the sample solution. Such a pre filtration system preferably includes a filter unit containing a filter with a pore size of 60 μm and a filter unit containing a filter with a pore size of 5 μm so that the sample solution is firstly filtered through the 60 μm filter unit, then the 5 μm filter unit before being filtered through filter unit 110 as described above.

Subsequent to the pre-filtration steps described above the method of detection of micro-organisms may be conducted as above described.

Figure 2B:
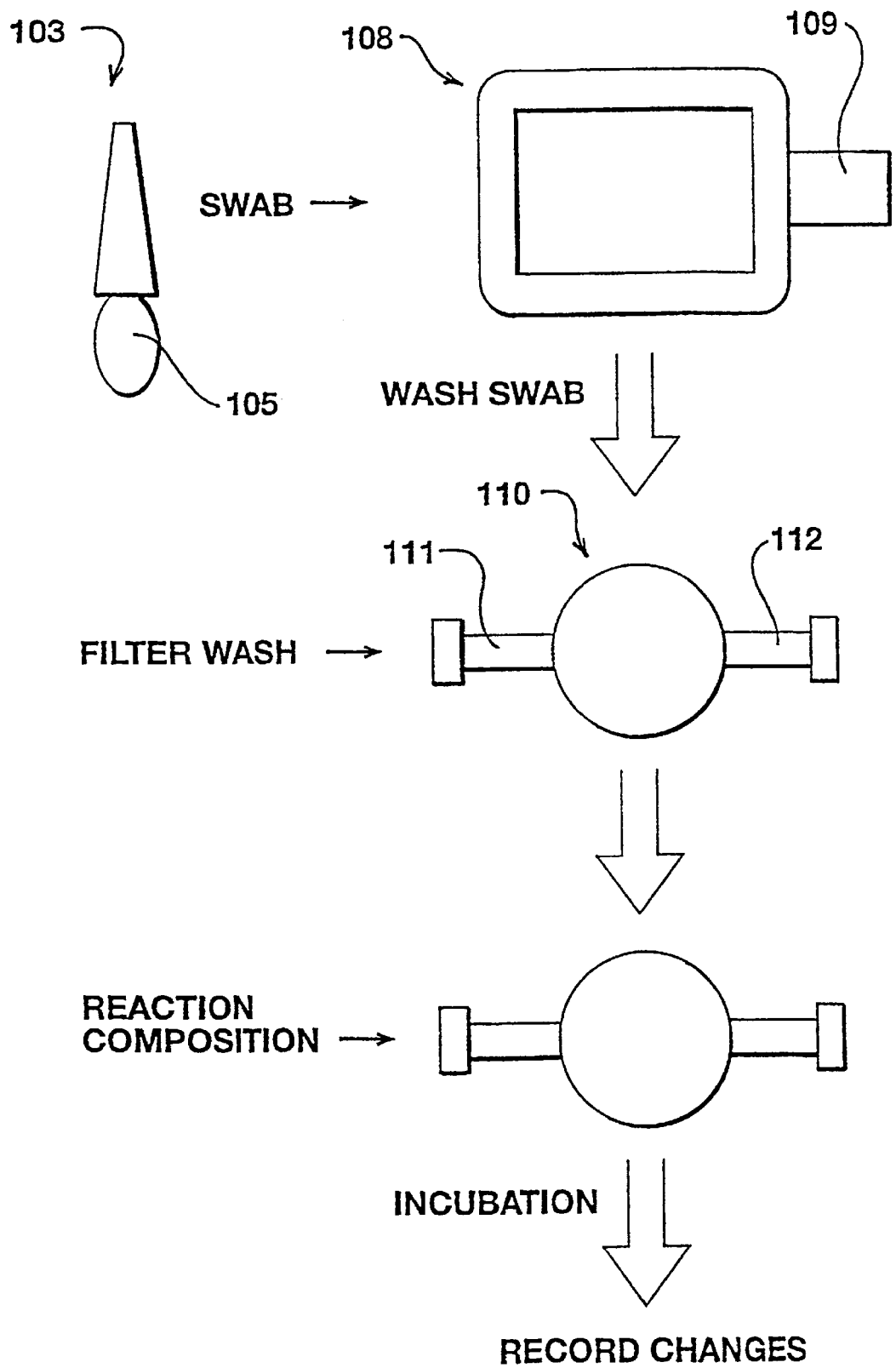

The method of detecting micro-organisms as described above may also include a first step of defining an area of the surface to be tested using a sterile template 108 as shown in FIG. 2B and according to the description of the first preferred embodiment Following placement of the template 108 a swab device 103 as described in first preferred embodiment may be used to take a sample from the defined area to be tested. This should be carried out in accordance with the method described in the first preferred embodiment. Subsequently the swab on the head 105 of swab device 103 may be washed in a suitable sterile solution and the resultant sample solution filtered through the filter unit 110.

Following filtration the test is conducted as herein described.

Third Preferred Embodiment

The preferred embodiments above described may include a further step at the conclusion of the assay of any of the above preferred embodiments in which the micro-organisms detected are typed in order to identify the type or class of micro-organisms present. Such a step is preferably conducted using enzyme-linked antibodies specific to a particular genus and/or species of micro-organism. Alternatively, a Fluorochrome labelled antibody may be utilised.

For example, in the case of the detection of micro-organisms being conducted in filtration unit 110 the filter unit is flushed with a volume of an appropriate buffer (Phosphate Buffered Saline (PBS), for example) to remove assay composition. Subsequently an appropriate amount of a solution containing enzyme-linked antibodies specific to a particular micro-organism may be inserted (preferably using an injection means or the like) into the filter unit 110. A stock solution of a particular enzyme-linked antibody to be used in this preferred embodiment contains 1.3 g of enzyme-linked antibody per liter of solution. Depending on the particular antibody being used this stock solution is then diluted to a working solution by factors of 1 in 500 to 1 in 5000. In this preferred embodiment of the invention the volume of enzyme-linked antibody is preferably from 0.2–2.0 ml. This volume may be altered to accommodate different sized filter units. If micro-organisms are present on the filter which specifically react with the enzyme-linked antibody added to the filter unit 110 the enzyme-linked antibody will be retained on the filter (ie bound to the micro-organisms present). If non-specific micro-organisms are present the enzyme-linked antibody will pass through the filter unit. Preferred enzymes to be linked to specific antibodies are Horse Radish Peroxidase (HRP) and Alkaline Phosphatase.

Following, insertion of the enzyme-linked antibody a substrate solution, specific to the enzyme-linked antibody, will be inserted into the filter unit 110. Such substrates are well known to those skilled in the art. For example, if an HRP linked antibody is used o Phenylenediamine would be utilised as a substrate; in the case of Alkaline Phospatase the substrate may be p Nitrophenyl phospate. The filter unit may subsequently be incubated and a change in the substrate solution recorded according to conventional techniques (for example a colour change). If a negative result is obtained (ie no change in the sample observed) subsequent enzyme-linked antibodies and appropriate substrates may be added to the filter unit 110 until a positive result is obtained indicating the micro-organism present in the original sample. The filter unit 110 should be flushed (with PBS for example) between each subsequent enzyme-linked antibody it inserted into the filter unit 110.

In an alternative to the above the enzyme-linked antibody solution is passed through the filter unit 110, collecting the filtrate in a container and subsequently adding an appropriate volume of a specific substrate to that container. If the micro-organisms present on the filter did not react with the enzyme-linked antibody solution passed through the filter unit 110 the enzyme-linked antibody would pass through the filter unit into the collecting container. On adding the substrate solution to the collecting container a positive result would be obtained indicating that particular micro-organism was not present within the filter unit 110.

In addition, more specific enzyme-linked antibody solutions may be added to the filter unit 110 or filtrate following a positive result in order to subtype the identified micro-organism.

It is preferred that the enzyme-linked antibody and substrate solutions be provided in sterile sealed containers, such as a plastic vial which may have a seal broken and then be squeezed to insert the solution therein into the filter unit 110 or a syringe.

In the case of the test of the present invention being conducted in a cuvette (as described in the first preferred embodiment and illustrated in FIGS. 1A and 1B) a sample of the reaction solution may be taken at the conclusion of the detection reaction. Such a sample may be drawn from the cuvette 100 through a sample port for example; this may obviate the need to open the vial which may contain a substantial number of pathogenic micro-organisms and thus may prevent contamination of the surrounding environment. Such a sample port may be present in the cap 102 in the case of that described in the first preferred embodiment with reference to FIG. 1A or in the base 107 of the head 105 in the case of the example illustrated in FIG. 1B. Once the sample is taken it may be combined with the enzyme-linked antibodies and substrate and typed by classical means to determine the species of micro-organism in the original sample. Finally, an anti-bacterial agent such as sodium hypochlorite can be added to decontaminate the test unit.

Where a Fluorochrome-linked antibody is used the same basic procedure is followed. However, there is no need for a substrate to be added to the filter or filtrate as Fluorochromes can be detected directly in the sample by monitoring their characteristic emission. Suitable Fluorochromes include Fluorescein and Rhodamine (tetramethylrhodamine isothiocyanate). In the case of using Fluorochromes it is preferable that the filtrate is used to determine the presence or absence of specific micro-organisms.

ADVANTAGES

The present invention utilises only a small volume of a assay composition to provide a relatively quick method of detecting micro-organisms on a variety of surfaces or in a variety of substances. It may also have the advantage that the components of the invention are such that they contain the microorganisms during the detection test and thus help prevent any further contamination.

In addition, a template may be provided which is adapted to standardise the area of the surface to be tested. This may be advantageous where comparison of results between tests is necessary.

Further, the present invention is easily applied to a number of environments and industries in which hygiene is of importance and contamination a problem; eg cosmetics preparation and manufacture, pharmaceutical preparation, laboratory environments, veterinary and surgical practices etc.

VARIATIONS

The composition of the present invention may be altered to support the growth and detection of micro-organisms other than those of the examples given in this specification without departing from the scope of the present invention.

It will also be appreciated that the pore size of the filters described in the preferred embodiments of this specifications may be altered for specific applications without departing from the scope of the invention.

The preferred embodiment describes the use of a sterile sampling instrument and a template which defines the area to be sampled and tested. It would be within the scope of the invention to have the sterile instrument to delineate the area to be sampled.

The composition of the present invention may be altered to support the growth and detection of micro-organisms other than coliform bacteria without departing from the scope of the present invention.

Finally it will be appreciated that various other alterations or modifications may be made to the foregoing without departing from the scope of the present invention.

We claim:

1. A method of detecting micro-organisms comprising the steps of taking a sample from a mass, surface or a fluid to be tested, providing a sealable sterile chamber of substantially limited volumetric capacity in which the detection process is to be conducted, placing the sample in contact with a composition capable of detecting micro-organisms within said sealable sterile chamber and recording a change in the composition.

2. The method of detecting micro-organisms as claimed in claim 1 wherein the volumetric capacity of said sealable sterile chamber is less than or equal to approximately 10 cubic centimeters.

3. The method of detecting micro-organisms as claimed in claim 2 wherein the volumetric capacity of said sealable sterile chamber is less than or equal to approximately 2 cubic centimeters.

4. The method of detecting micro-organisms as claimed in claim 1 wherein the sample is taken and is placed in contact with said composition in said sealable sterile chamber using a sterile sampling instrument.

5. The method of detecting micro-organisms as claimed in claim 1 wherein at least a part of the sealable sterile chamber is transparent and the change in the composition capable of detecting micro-organisms is one which can be visualised by eye or in a spectrophotometer.

6. The method of detecting micro-organisms as claimed in claim 1 wherein the method further comprises any one or more of the following steps: delineating an area of a surface to be tested and placing the sterile sampling instrument in contact with substantially all of the delineated area, removing any extraneous matter from said sample prior to conducting to placing the sample in contact with the composition adapted to detect micro-organisms, and typing any micro-organisms detected after recording a change in the composition adapted to detect micro-organisms.

7. The method of detecting micro-organisms as claimed in claim 1 wherein the method comprises the steps of taking a sample from a mass, surface or a fluid to be tested, providing a sealable sterile chamber, placing the sample in the sealable sterile chamber, substantially isolating any micro-organisms present in the sample by filtration within the sealable sterile chamber, placing the isolated micro-organisms in contact with a composition capable of detecting microorganisms within sealable sterile chamber, and recording a change in the composition.

8. The method of detecting micro-organisms as claimed in claim 1 wherein the method comprises the steps of providing a delineating instrument, delineating an area of a surface to be tested, providing a sterile sampling instrument, placing the sterile sampling instrument in contact with substantially the whole of the delineated area to be tested, washing said sterile sampling instrument in an appropriate solution, providing a sealable sterile chamber, placing the wash solution in said sealable sterile chamber, substantially isolating any micro-organisms present in the wash solution by filtration within the sealable sterile chamber, placing the isolated micro-organisms in contact with a composition capable of detecting micro-organisms within sealable sterile chamber, and recording a change in the composition.

9. The method of detecting micro-organisms as claimed in claim 1 wherein the method comprises the steps of providing a sterile sampling instrument, taking a sample of from a mass, liquid or surface to be tested, providing a sealable sterile chamber containing a defined amount of a composition capable of detecting micro-organisms, placing at least a part of the sterile sampling instrument and thus the sample in contact with the composition, and recording a change in the composition.

10. The method of detecting micro-organisms as claimed in claim 1 wherein the method comprises the steps of providing a delineating instrument, delineating an area of a surface to be tested, providing a sterile sampling instrument, placing the sampling instrument in contact with substantially the whole of the delineate area of the surface to be tested, providing a sealable sterile chamber containing a defined amount of a composition capable of detecting micro-organisms, placing at least a part of the sterile sampling instrument and thus the sample in contact with the composition, and recording a change in the composition.

11. A kit for the detection of micro-organisms according to the method claimed in claim 1 comprising a sealable sterile chamber, a defined amount of a composition adapted to detect micro-organisms, and a means for collecting and placing a sample in contact with said composition adapted to detect micro-organisms.

* * * * *